United States Patent
Menten et al.

(10) Patent No.: US 8,365,598 B2
(45) Date of Patent: Feb. 5, 2013

(54) DEVICE AND METHOD FOR QUALITY TESTING SHEET METAL PARTS

(75) Inventors: Rainer Menten, Moritzburg (DE); Bernd Schneegast, Ilmenau (DE); Christian Licht, Stuttgart (DE); Hans-Stefan Heimberger, Muehlacker (DE); Timo Uhlig, Dresden (DE); Andreas Eichler, Dresden (DE); Horst Jonuscheit, Dormitz (DE)

(73) Assignees: Dr. Ing. h.c. F. Porsche Aktiengesellschaft (DE); KWD Automobiltechnik Karosseriewerke Dresden GmbH (DE); Medav GmbH (DE)

( * ) Notice: Subject to any disclaimer, the term of this patent is extended or adjusted under 35 U.S.C. 154(b) by 236 days.

(21) Appl. No.: 12/808,075

(22) PCT Filed: Nov. 22, 2008

(86) PCT No.: PCT/EP2008/009919
§ 371 (c)(1),
(2), (4) Date: Sep. 2, 2010

(87) PCT Pub. No.: WO2009/074220
PCT Pub. Date: Jun. 18, 2009

(65) Prior Publication Data
US 2010/0326195 A1 Dec. 30, 2010

(30) Foreign Application Priority Data
Dec. 12, 2007 (DE) .......................... 10 2007 060 278

(51) Int. Cl.
*G01M 7/06* (2006.01)

(52) U.S. Cl. .......................................... 73/579; 73/663
(58) Field of Classification Search .................... 73/579, 73/587, 663
See application file for complete search history.

(56) References Cited

U.S. PATENT DOCUMENTS 3,023,609 A * 3/1962 Schubring ........................ 73/579
3,580,056 A * 5/1971 Warner ........................... 73/579
(Continued)

FOREIGN PATENT DOCUMENTS

| DE | 293 428 | 8/1991 |
|---|---|---|
| DE | 42 07 728 | 9/1993 |
| DE | 42 42 442 | 6/1994 |
| DE | 10 2004 031 184 | 10/2005 |
| EP | 0 217 758 | 4/1987 |
| GB | 2 340 604 | 2/2000 |
| JP | 63250548 A * | 10/1988 |

*Primary Examiner* — Peter J Macchiarolo
*Assistant Examiner* — Rose M Miller
(74) *Attorney, Agent, or Firm* — Gerald E. Hespos; Michael J. Porco

(57) ABSTRACT

A device and a method are provided for quality testing sheet metal parts, particularly deep-drawn parts. The device has a pulse generator (20) that excites the sheet metal part (2) to oscillate, a sound sensor (19) that picks up the sound profile, and an evaluation unit that compares the recorded sound profile with a reference curve and generates a signal with which the sheet metal parts are classified. To increase the suitability of a generic device or generic method for use in an automated production system, a testing device (4) is integrated into a press line in a clock cycle controlled fashion. Sheet metal parts whose recorded sound profile does not lie in a tolerance range of the reference curve can be eliminated by a sorting device.

13 Claims, 4 Drawing Sheets

U.S. PATENT DOCUMENTS

| | | | | |
|---|---|---|---|---|
| 3,623,358 A | * | 11/1971 | Sugimoto | 73/579 |
| 3,733,890 A | * | 5/1973 | Landvogt | 73/579 |
| 4,283,952 A | * | 8/1981 | Newman | 73/579 |
| 4,722,223 A | * | 2/1988 | Bach et al. | 73/579 |
| 5,216,921 A | * | 6/1993 | Tsuboi | 73/579 |
| 5,448,902 A | | 9/1995 | Thoms et al. | |
| 6,397,680 B1 | * | 6/2002 | Levesque et al. | 73/602 |
| 7,984,649 B2 | * | 7/2011 | Kono et al. | 73/579 |

* cited by examiner

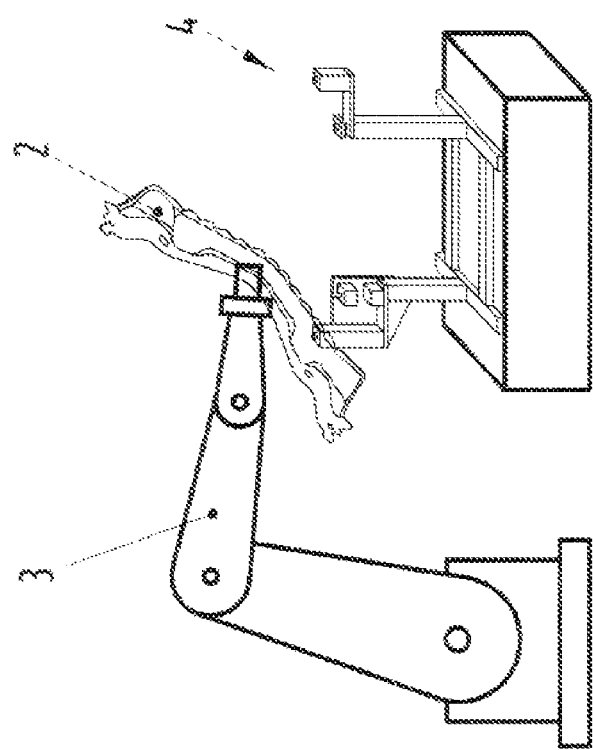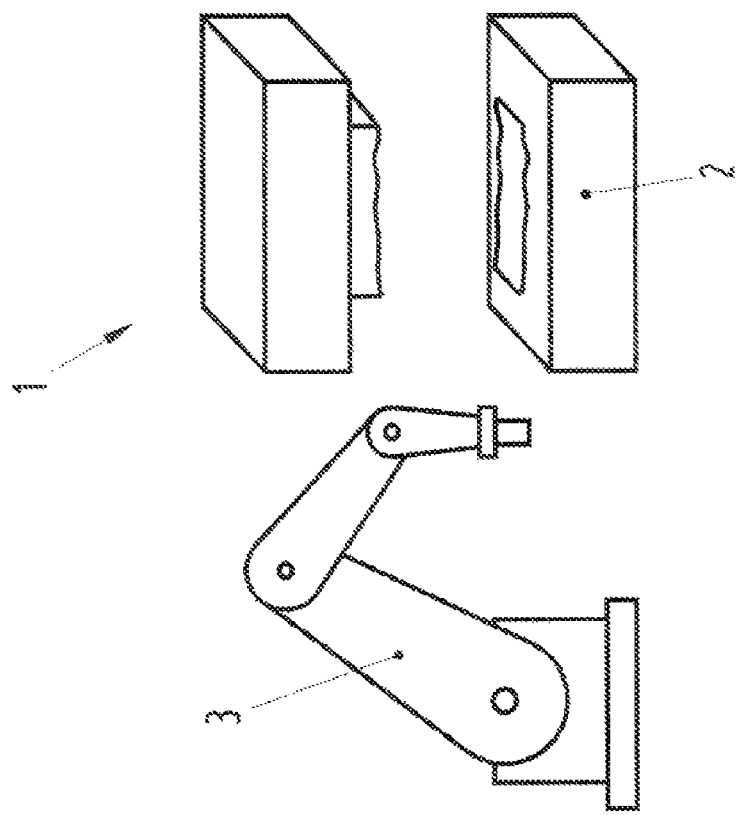
Fig. 1

DEVICE AND METHOD FOR QUALITY TESTING SHEET METAL PARTS

CROSS REFERENCE TO RELATED APPLICATIONS

This application is the U.S. national phase of PCT/EP2008/009919 filed on Nov. 22, 2008, which claims priority on German Patent Appl. No. 10 2007 060 278.4 filed on Dec. 12, 2007, the entire disclosures of which are incorporated herein by reference.

BACKGROUND OF THE INVENTION

1. Field of the Invention

The invention relates to a device and a method for quality testing sheet metal parts.

2. Description of the Related Art

In the series production of vehicles it is customary to test the quality of sheet metal parts for the bodywork, particularly of deep-drawn parts, before installation. Particularly in the case of deep-drawn parts with large depths, fractures or constrictions may occur on the sheet metal part when, for example, tool changes occur or there are fluctuations in the sheet metal thickness. If these sheet metal parts which are subject to faults are processed further, the expenditure on post-processing is increased, DE 42 07 728 A1 discloses a method for quality testing test specimens by exciting the test specimen and evaluating the measured sound curve. The sound curve is evaluated by means of a neuronal network which has been learnt in a training phase on the basis of a selected set of test specimens.

The object of the invention is to increase the suitability of the generic method or the generic device for automated use in the series production of vehicles.

SUMMARY OF THE INVENTION

A device is provided for quality testing sheet metal parts which comprises a testing device and a sorting device. The testing device has a pulse generator which excites the sheet metal part to oscillate, and these oscillations are subsequently recorded by a sound sensor as a sound curve. An evaluation unit of the testing device compares the recorded sound profile with a reference curve and generates a signal with which the sheet metal parts can be classified. According to the invention there is provision that the testing device is integrated into a press line in a clock cycle controlled fashion. That is to say the clock cycle which is to be found in the press line is preferably also complied with at the testing device. For this purpose, the testing device is arranged downstream of the last press stage and is supplied with sheet metal parts from the last press stage in a clock cycle controlled fashion. Within one clock cycle, the quality of the sheet metal part is therefore tested with the device according to the invention. The sheet metal parts are for this purpose inserted into the testing device in accordance with the claimed method according to claim 11. In this context, the insertion can be carried out by means of a robot. After the insertion into the testing device, the sheet metal part is excited to oscillate and the sound sensor picks up the sound curve. If the evaluation unit determines that the recorded sound profile does not lie in the tolerance range of the reference curve, the sheet metal part is eliminated from the process by a sorting device.

In one embodiment, the testing device can comprise a frame which is attached to a floor or to a machine part so as to be decoupled from oscillations. This has the advantage that surrounding oscillations do not adversely affect the measuring process or falsify the measurement results.

The oscillation decoupling means can preferably be embodied as an elastomer bearing and is secured to feet which are attached to the floor or to the machine part. It is possible to mount the testing device either on the floor of the hall or on a press which is not involved in the shaping process. If the testing device is itself mounted on a press, this has the advantage that a robot which is present in any case between two presses can be used as the feed device. Furthermore, the testing device can be easily retrofitted into any existing press line. Alternatively, the testing device can be supplied by an operator who removes the completely deep-drawn sheet metal part from the last press stage of the press line arranged upstream and inserts it into the testing device.

There is provision that during the recording of the sound curve the sheet metal part is mounted on at least two receptacles of the testing device. The number of support points should be selected as a function of the size of the sheet metal part which is to be tested. However, more than three support points are not recommended in view of the unimpeded oscillation of the sheet metal part.

If the at least two receptacles are spaced apart from one another at a distance which corresponds to the major part of the length or width of the sheet metal part, the oscillations of the sheet metal part can propagate in an optimum way and be correspondingly recorded.

A second oscillation decoupling means may be provided by virtue of the fact that the receptacles for the sheet metal part are oscillation-decoupled from the frame.

For this purpose, a receptacle bolt can penetrate the receptacles which are constructed from elastomer.

In order to facilitate the insertion of the sheet metal part into the testing device, the receptacle bolt can be of rounded design.

The sound sensor can preferably be arranged in the vicinity of one of the receptacles, so that both the receptacle and the sound sensor can be attached to a common carrier.

The pulse generator can be arranged in the vicinity of the other receptacle, so that a common carrier for the pulse generator and receptacle can also be provided here.

A high degree of automization can be achieved if a feed device receives the sheet metal part from the press line arranged upstream. If the feed device is a robot, the feed device can automatically feed the sheet metal part to the testing device.

The feed device transfers the received sheet metal part from the last press stage in the direction of the testing device and places it on two receptacle bolts there.

The pulse generator preferably excites the sheet metal part resting on the two receptacle bolts to oscillate, during which the sound curve is recorded by the sound sensor. The recording should already start shortly before the excitation in order to record an excited state. The recording period can in principle be freely selected within the scope of the predefined clock time, wherein the duration of the calculation time and the removal by the sorting device also have to be taken into account. It has become apparent that a recording period of 1 second is sufficient to differentiate a fault-free part from a faulty part. It is possible to provide that the sheet metal part is excited multiply, i.e. at a plurality of points. A multiple impact is appropriate if a single impact location is not sufficient owing to the excitation and propagation of the oscillations. The reasons for this are possibly the size of the surface area of the sheet metal part, rigidities, rotational symmetry of components or the like. The individual impacts may be evaluated separately (for example comparison for each impact location separately and subsequent overall evaluation) or cumulatively (for example addition of the individual spectra).

The recorded sound curve can be compared in an evaluation unit with a reference curve in an evaluation unit. The evaluation unit outputs, in accordance with the result, a signal with which the sheet metal part can be classified.

If the recorded sound curve lies within the permitted and previously defined reference curve, the part is free of faults. The sheet metal part can be transferred from the sorting device to the next processing station, for example to the dispatching station.

If the recorded sound curve lies outside the tolerance range of the reference curve, the sheet metal part is transferred from the sorting device to an intermediate station. The intermediate station may be, for example, a storage stack or a warehouse.

The eliminated sheet metal parts of the intermediate station can subsequently be subjected to a second, more precise quality testing means. This testing may be performed manually.

Further advantageous refinements of the invention are explained in more detail below with reference to the drawing.

BRIEF DESCRIPTION OF THE DRAWINGS

FIG. 1 shows a schematic illustration of a press line with an integrated testing device.

DETAILED DESCRIPTION OF THE PREFERRED EMBODIMENT

Figure 2:
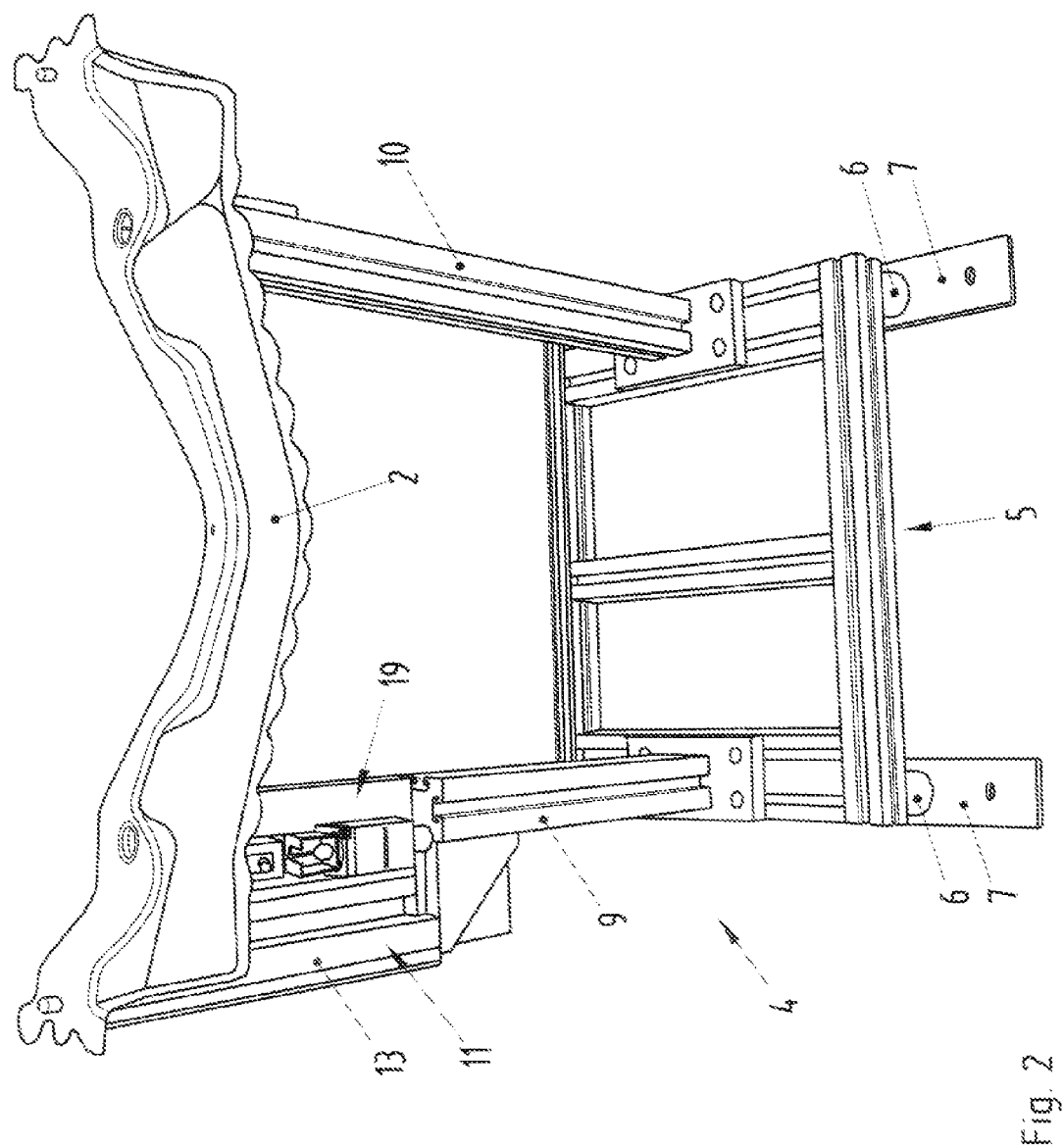
FIG. 2 shows a testing device with a sheet metal part in a view from obliquely above.

FIG. 1 shows a schematic arrangement of the components of a press line. Shaping a transverse carrier shell with a large drawing depth requires a plurality of presses 1 arranged one behind the other and supplied with sheet metal parts 2 in a corresponding clock cycle time. The handling of the sheet metal parts 2 from press to press is carried out fully automatically with robots 3. Only the last press stage 1, with the adjoining testing device 4, of the press line is illustrated in FIG. 1. For the invention it is irrelevant whether the press line is operated fully automatically or manually. What is important is that the quality of the shaping process at the end be tested in a clock cycle controlled fashion by the testing device 4, i.e. within the predefined clock cycle of the press line.

The testing device 4 can be integrated into a press and therefore retrofitted in any press line. The testing device 4 comprises, according to FIGS. 2 and 3, a frame 5 which is secured to feet 7 by means of elastomer bearings 6. Using the feet 7, the testing device 4 is either attached to a carrier 8 on the floor of the hall or attached to an actual press which is not involved in the shaping process. The elastomer bearings 6 serve to decouple oscillation of the testing device 4 from the press or the floor of the hall. Supporting pillars 9 and 10, which serve to receive the sheet metal part 2, protrude from the frame 5. For this purpose, in each case a securing bracket 11 or 12 is attached to the upper end of the supporting pillar 9 or 10. An elastomer receptacle 15, 18 protrudes from perpendicularly extending limbs 13 and 14 of the securing brackets 11 and 12, in which receptacle 15, 16, a receptacle bolt 17, 18 is arranged in a countersunk fashion. The receptacle bolt 17, 18 is of rounded design at the top in order to facilitate the fitting on or threading in of the sheet metal part 2. During the testing process, the receptacle bolts 17, 18 penetrate bores which are present in any case in the sheet metal part 2 so that the sheet metal part 2 rests on two support points which are arranged relatively far apart from one another. Good oscillation decay behavior after the excitation of the sheet metal part 2 is therefore possible. The left-hand securing bracket 11 additionally holds a sound sensor 19, while the pulse generator 20 is arranged on the securing bracket 12.

Figure 3:
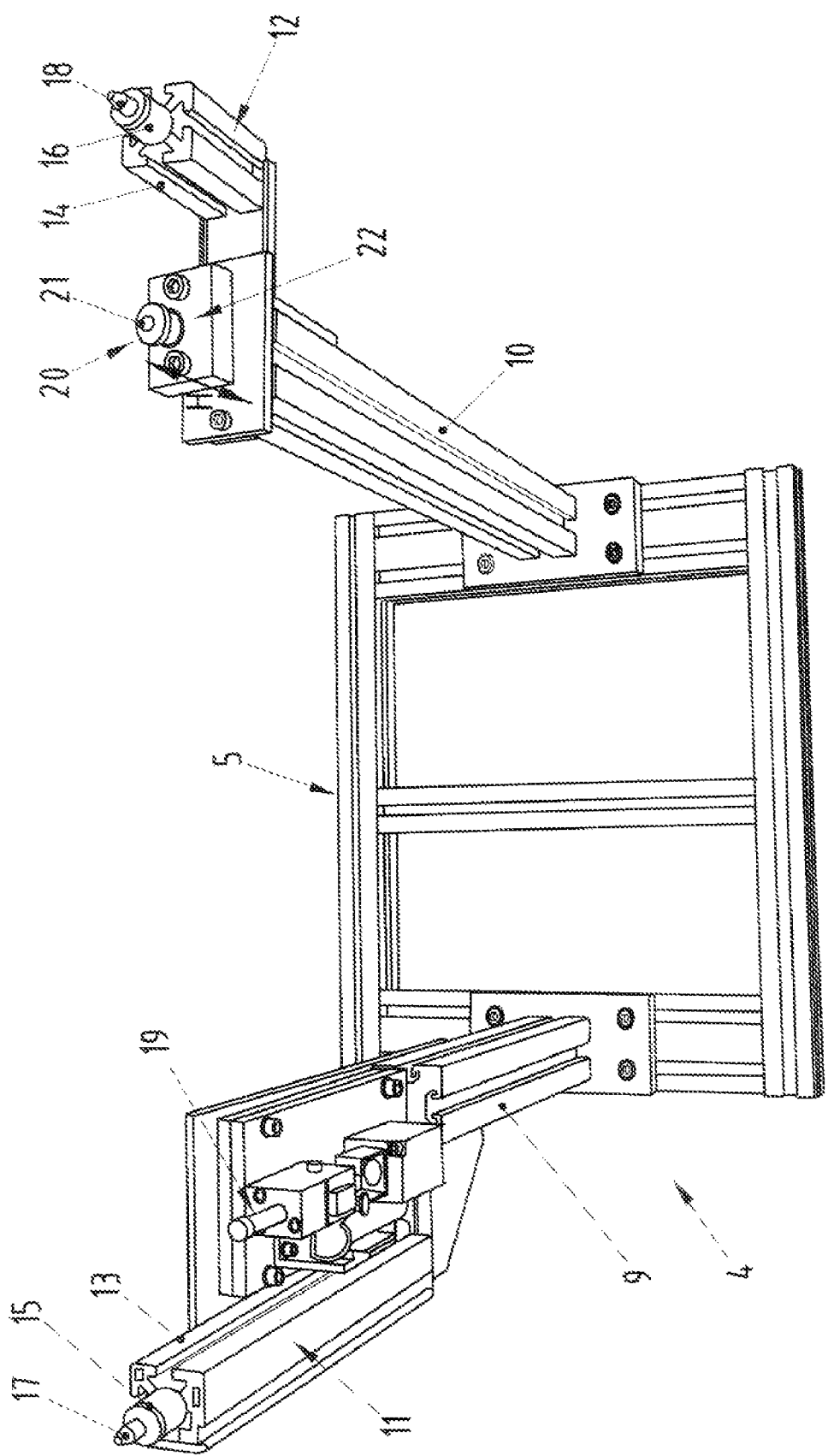
FIG. 3 shows a testing device without a sheet metal part according to FIG. 2.

As is apparent from FIG. 3, the pulse generator 20 comprises a plunger 21 which is extended in the direction of the arrow H, by means of a reciprocating device or impacting device 22 in order to excite oscillations in the sheet metal part 2. The control commands for the reciprocating device 22 are issued by a central control unit. In this context, the control system can, on the one hand, receive an enable trigger from the control system controller by means of the measurement system. On the other hand, the system controller can receive a trigger if the sheet metal part 2 is positioned and free.

The reciprocating device 22 may operate in a hydraulic or pneumatic fashion, but can also be driven electrically.

Figure 4:
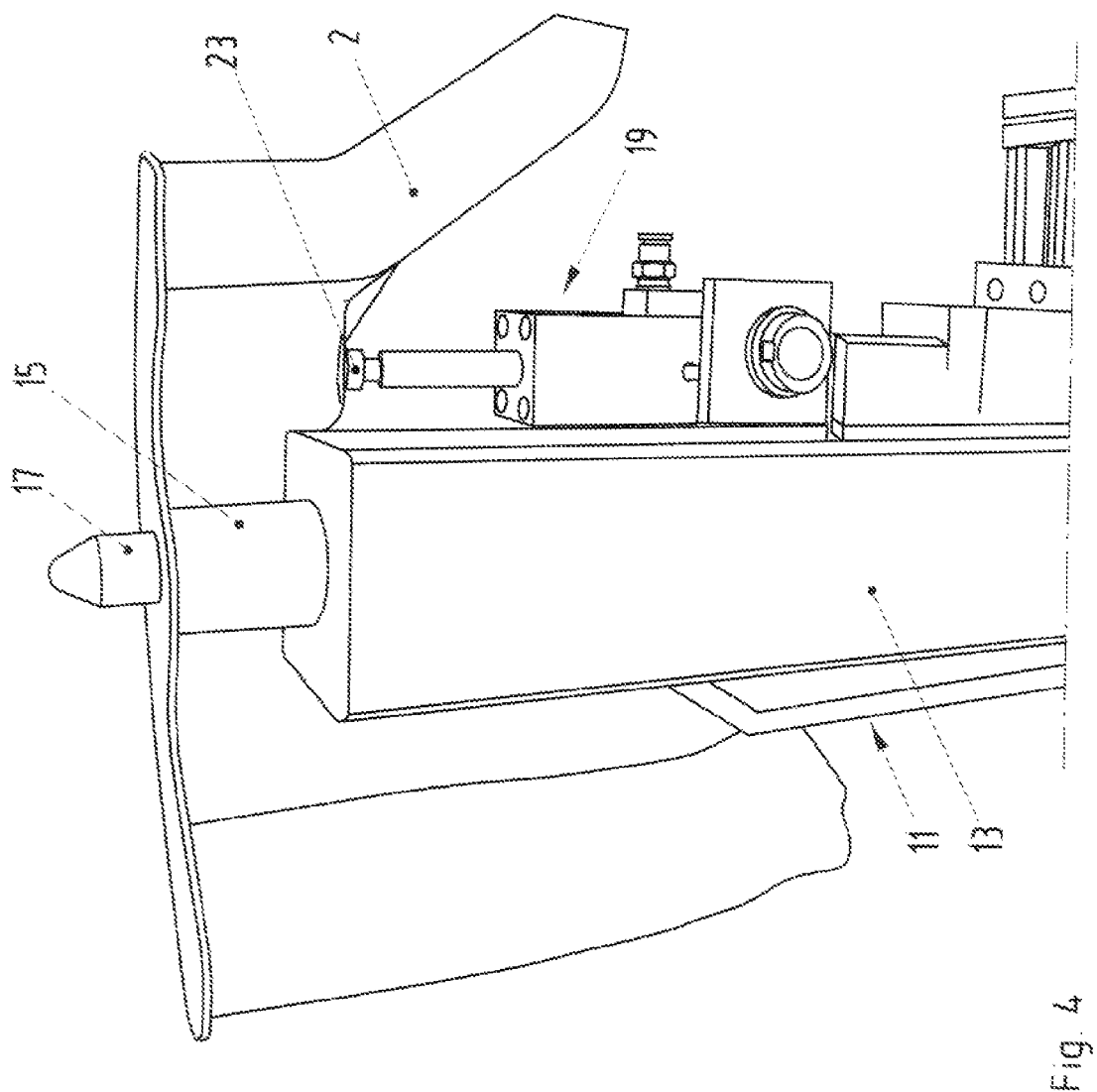
FIG. 4 shows a receptacle with a sound sensor according to FIG. 2 in a perspective side view.

As is apparent from FIG. 4, the sound sensor 19, which picks up the oscillations of the sheet metal part 2 generated by the plunger 21, is attached to the securing bracket 11. The sound sensor 19 is likewise connected to the control unit in terms of data technology. If possible, the sound sensor 19 is to be arranged on the sheet metal part 2 in such a way that the solid-borne sound waves can be picked up in an unimpeded fashion. In the exemplary embodiment shown, the sound sensor 19 is arranged underneath a half shell of the sheet metal part 2 which is open in the downward direction. In this context, the sound sensor 19 bears with its sensing tip 23 directly on the sheet metal part 2. The recording of the signal starts just before the excitation with the plunger 21. The duration of the recording depends on the clock cycle time of the press line. It is possible to draw conclusions about the quality of the sheet metal part with a recording which does not last longer than one second. The recording should at best last until the oscillations have almost decayed completely.

A solid-borne sound sensor which bears with a sensing tip 23 against the sheet metal part 2 can be used as the sound sensor 19. Alternatively, a microphone is conceivable as a sound sensor if the ambient noise is not so strong that it influences the measurement result. Further alternative oscillation sensors may be a laser vibrator, an ultrasound sensor or a radar sensor, these being respectively suitable for the oscillation measurement. It is important here that these sensors measure the oscillation in a contactless fashion, which provides advantages in terms of the mass reaction and the positioning times. A possible general summary is that all the sensors and measuring principles in which the oscillation travel, the oscillation speed or oscillation acceleration is measured and the acquired signal is suitable for frequency evaluation are suitable.

The recorded signals are transmitted to the central control unit and evaluated. The evaluation takes place in an evaluation unit by means of comparisons with a known sound profile. This reference curve is created in advance of the actuation of the testing device 4 by what is referred to as a learning process. On the basis of a significant number of visually assessed sheet metal parts 2 which are characterized as "OK" and "not OK" parts, it is possible to define a curve with a corresponding tolerance range. If the measured sound curve lies outside of the tolerance range, this sheet metal part is eliminated as a not OK part. This is done by the evaluation unit issuing a signal to the sorting device which may be, for example, a robot arranged downstream. This robot either passes on the OK parts to the subsequent stations or deposits the not OK part on a stack. The not OK parts can be tested manually once more in a further method step. If not OK parts build up, feedback can be provided to the machine controller. Furthermore, not OK parts can be subsequently visually inspected and parts which can still be post-processed can be filtered out.

The method for quality testing deep-drawn sheet metal parts with the above-described device is configured as follows:

An operator or a robot receives the sheet metal part 2 from the last press stage and inserts it into the receptacles of the testing device 4. The plunger 21 of the pulse generator 20 excites the sheet metal part 2 resting on the two support points to oscillate, while the sound curve is recorded by the sound sensor 19. If a comparison of the recorded sound curve with the reference curve reveals that the sheet metal part 2 lies outside the tolerance range of the reference curve, the sheet metal part 2 is eliminated from the production process by a sorting device which can either be a robot or an operator.

The invention claimed is:

1. A device for quality testing sheet metal parts with a testing device, comprising:
   a frame having at least two receptacles for mounting the sheet metal part,
   a pulse generator that excites the sheet metal part to oscillate,
   an elastomer bearing attached to the frame and to feet secured on a floor or on a machine part so as to decouple oscillations of the sheet metal part from the floor or the machine part,
   a sound sensor that picks up a sound profile caused by the oscillations of the sheet metal part, and
   an evaluation unit that compares the recorded sound profile with a reference curve and generates a signal with which the sheet metal parts are classified,
   characterized in that sheet metal parts can be fed to the testing device in a clock cycle controlled fashion, wherein sheet metal parts whose recorded sound profile does not lie in a tolerance range of the reference curve can be eliminated by a sorting device.

2. The device as claimed in claim 1,
   characterized in that the at least two receptacles are spaced apart from one another at a distance that corresponds to a major part of a length or width of the sheet metal part.

3. The device as claimed in claim 1,
   characterized in that the receptacles are oscillation-decoupled from the frame.

4. The device as claimed in claim 3,
   characterized in that the receptacles are constructed from elastomer and receptacle bolts penetrate the receptacles.

5. The device as claimed in claim 4,
   characterized in that the receptacle bolts are of rounded design.

6. The device as claimed in claim 2,
   characterized in that the sound sensor arranged in a vicinity of one of the receptacles.

7. The device as claimed in claim 2,
   characterized in that the pulse generator is arranged in a vicinity of one of the receptacles.

8. A method for quality testing sheet metal parts with a testing device, comprising:
   using a feed device for feeding the sheet metal parts in a clock cycle controlled fashion from a press line arranged upstream to the testing device,
   placing the sheet metal part on two receptacle bolts of the testing device,
   employing a pulse generator for exciting the sheet metal part to oscillate,
   picking up a sound profile of the oscillating sheet,
   comparing the sound profile with a reference curve and generating a signal with which the sheet metal parts are classified, and
   eliminating the sheet metal parts whose recorded sound profile does not lie in a tolerance range of the reference curve.

9. The method as claimed in claim 8,
   characterized in that the pulse generator excites the sheet metal part resting on the two receptacle bolts to oscillate, during which the sound profile is recorded by a sound sensor.

10. The method as claimed in claim 9,
    characterized in that the recorded sound profile is compared with a reference curve in an evaluation unit.

11. The method as claimed in claim 10,
    further comprising: transferring the sheet metal part to a subsequent processing station if the recorded sound profile lies within the reference curve.

12. The method as claimed in claim 10,
    further comprising: transferring the sheet metal part to an intermediate station if the recorded sound profile lies outside the reference curve.

13. The method as claimed in claim 12,
    further comprising: subjecting the sheet metal parts that have been transferred to the intermediate station to a second quality testing means.

* * * * *